United States Patent [19]

Colvin, Jr.

[11] Patent Number: 4,891,133

[45] Date of Patent: Jan. 2, 1990

[54] CHROMATOGRAPHY APPARATUS

[75] Inventor: Arthur E. Colvin, Jr., Mount Airy, Md.

[73] Assignee: Cerex Corporation, Gaithersburg, Md.

[21] Appl. No.: 96,506

[22] Filed: Sep. 15, 1987

[51] Int. Cl.$^4$ ............................................. B01D 15/08
[52] U.S. Cl. ................................. 210/198.2; 210/188; 210/456; 210/510.1; 55/386
[58] Field of Search ............ 210/656, 658, 659, 198.2, 210/180, 188, 750, 510.1, 456; 55/386

[56] References Cited

U.S. PATENT DOCUMENTS

| | | | |
|---|---|---|---|
| 3,024,913 | 3/1962 | Edmunds | 210/510.1 |
| 3,049,796 | 8/1962 | Pall | 210/510.1 |
| 3,487,938 | 1/1970 | Patterson | 210/198.2 |
| 3,510,271 | 5/1970 | Emneus | 210/198.2 |
| 3,539,505 | 11/1970 | Lauer | 210/198.2 |
| 3,966,609 | 6/1976 | Godbille | 210/198.2 |
| 4,061,031 | 12/1977 | Grimsrud | 210/188 |
| 4,113,627 | 9/1978 | Leason | 264/251 |
| 4,208,279 | 6/1980 | Varani | 210/180 |
| 4,350,595 | 9/1982 | Gunkel | 210/198.2 |
| 4,354,932 | 10/1982 | McNeil | 210/198.2 |
| 4,361,482 | 11/1982 | Teetz | 210/198.2 |
| 4,399,032 | 8/1983 | Mott | 210/510.1 |
| 4,469,597 | 9/1984 | Mott | 210/198.2 |
| 4,512,897 | 4/1985 | Crowder | 210/198.2 |
| 4,549,584 | 10/1985 | Morin | 210/198.2 |
| 4,564,450 | 1/1986 | Piper | 210/510.1 |
| 4,582,608 | 4/1986 | Ritacco | 210/656 |
| 4,597,866 | 7/1986 | Couillard | 210/198.2 |
| 4,636,315 | 1/1987 | Allen | 210/198.2 |
| 4,675,104 | 6/1987 | Rai | 210/198.2 |

OTHER PUBLICATIONS

Random House Dictionary of the English Language, New York Random House 1966, p. 114.

Primary Examiner—Ernest G. Therkorn
Attorney, Agent, or Firm—Michael W. York

[57] ABSTRACT

Liquid chromatography apparatus including a hollow cylinder and a fixed end closure in which the effective useful length of the cylinder is varied through the use of a piston member that slides within the cylinder due to force exerted by a threaded shaft that is connected to a handle. Binding of the piston member in the cylinder is prevented by a ball joint that operatively connects the piston member to the threaded shaft and by a plurality of O-rings located on the piston member that contact the inner wall of the cylinder and tend to prevent tipping of the piston member. Even liquid distribution and filtering is obtained through a 0.5 micron porous sintered stainless steel liquid distribution disk. A smooth inclined surface in combination with an uninterrupted ring provide a trap for bubbles of gas located inside the cylinder. A composite porous segmented sintered liquid distribution disk is also presented that is particularly useful for large scale liquid chromatography as is the method of manufacturing the composite segmented disk.

5 Claims, 2 Drawing Sheets

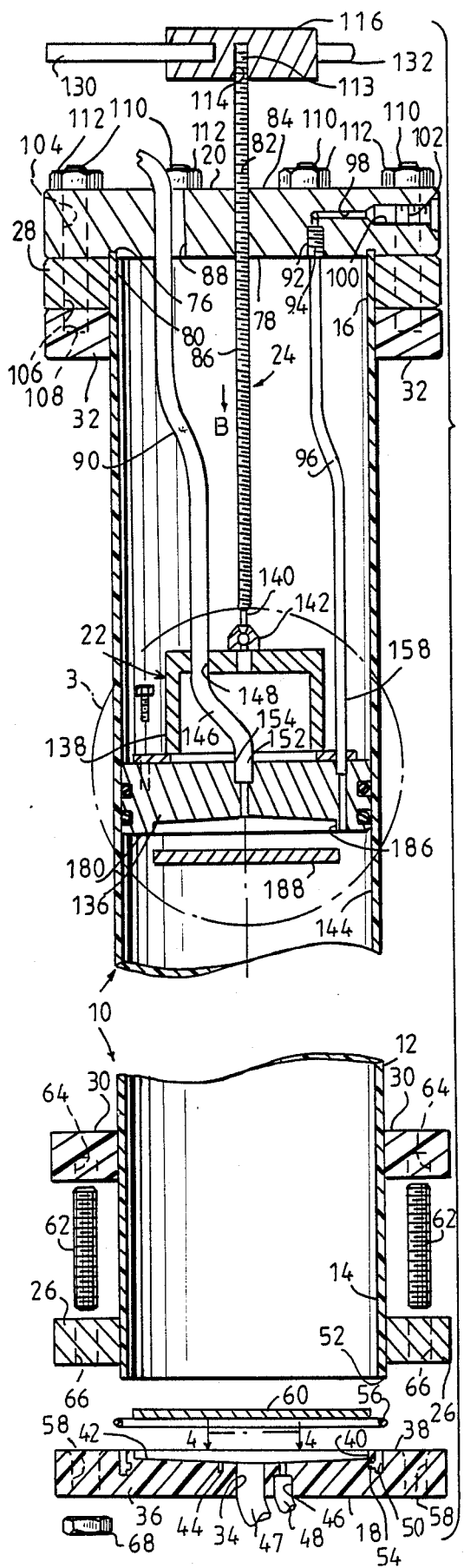

CHROMATOGRAPHY APPARATUS

BACKGROUND OF THE INVENTION

Frequently it is desirable to separate out one or more components that are useful from a fluid mixture that contains other components that may not be useful or are less valuable or less useful. To accomplish this it is often necessary or desirable to fractionate such a fluid mixture to separate out the useful or desired components. This has been accomplished through the use of liquid chromatography systems. Unfortunately, previous liquid chromatography systems have a number of problems or disadvantages.

One of these problems is related to fluid control. In this connection, the control of fluid flow is of primary importance in the field of liquid chromatography. In a liquid chromatography system a fluid, usually comprising a carrier fluid and a sample fluid, is injected into a separation column, as the fluid passes through the column the constituents of the sample fluid travel at different velocities due to their various rates of interaction with the packing material of the column. The result of this procedure is an output flow of the various individual constituents one after the other and consequently the output of the column would initially contain only the least retained constituent and etc. Ideally, there would be a sharp cut off at the interface between constituents. However, in practice this has not always been the case and the transition from one constituent of the sample fluid to the next is often gradual and indistinct resulting in inefficient separation of the constituents.

This transition problem between constituents can result from the fact that, in many columns, the fluid flow along the column is usually confined to a core portion of the column-packing material. The inefficiency arises because the core segment quickly becomes saturated and constituents which should be slowed after traveling a certain length along the columns continue to flow since they cannot interact with the saturated packing material of the core segment. Thus the output of the constituents at the transitions are blended and indistinct. The capacity of the column for increased loads of the sample constituents is also significantly reduced since only the core portion of the packing material is being utilized.

The constrained fluid flow through a liquid chromatography column also reduces the useful life of that column. The useful life of a given packing material is finite since, when a fluid is passed over the packing material a small amount of the constituents of that fluid may be irreversibly retained. Consequently, for a given cross-section of packing material if all the fluid passed is confined to a core segment the useful life of that cross-section of material is less than if the same amount of fluid were distributed across the entire cross-section.

Another problem associated with column chromatography is the inability to readily scale up the size of usable systems. Column chromatography has become an accepted conventional laboratory method for use in the separation of materials. However, when attempts are made to use this method on a large scale, a number of difficulties arise which have previously rendered the practicability of large scale column chromatography questionable. Particularly serious difficulties arise with increasing length and diameter of the columns, by the distortion of the fronts between constituents which leads to a poor utilization of the column capacity, and, especially in the case of low separation factors, to the impossibility of adaptation to large scale separation of the multi-component liquid.

The distortion of the fronts is due to a great variety of different factors, such as nonuniform filling of the column and fluid distribution, variations in temperature, viscosity and volume, channel formation, and the like. Thus, whereas in the ideal case, the concentration time diagram of a liquid which has passed through a chromatographic column represents a more or less steep bell-shaped curve, in the case of columns used for large scale chromatography, this diagram degenerates into drawn out shapes.

There have also been problems associated with filling the column chromatography unit with packing material and removing bubbles of air and other gasses from liquid in the column. In this connection, in a fixed length column it is very difficult to properly pack the column with just the right amount of packing material and an incorrectly packed column can prevent the proper separation of the constituents passing through the column. Although the length of the column has been allowed to be varied by the use of a variable position end such as a plunger, there have been problems associated with its proper use. It has also been difficult to remove bubbles from the liquid that is introduced into a packed column and the presence of bubbles can interfere with the proper operation of the column.

This invention overcomes these previous problems associated with column chromatography and provides for the proper control of liquid flow for the effective separation of the constituents, provides an effective plunger, allows the unit to be increased in size without loss of effectiveness and allows gas bubbles to be effectively removed from liquid in the column.

BRIEF DESCRIPTION OF THE INVENTION

This invention relates to liquid separation apparatus and more particularly to chromatographic apparatus.

It is accordingly an object of the invention to provide chromatography apparatus that has increased separation efficiency.

It is an object of the invention to provide chromatography apparatus that effectively separates liquids.

It is an object of the invention to provide chromatography apparatus that has provisions for effective liquid control.

It is an object of the invention to provide fluid chromatography apparatus that has simple provisions for liquid control.

It is also an object of the invention to provide chromatography apparatus that is capable of being effectively scaled up in size.

It is also an object of the invention to provide chromatography apparatus that is well adapted for large scale use.

It is also an object of the invention to provide chromatography apparatus that does not require a fixed length packing column.

It is an object of the invention to provide chromatography apparatus that is usable with packing columns of various lengths.

It is an object of the invention to provide variable column length chromatography apparatus that is readily adjustable for various column lengths.

It is an object of the invention to provide variable column length chromatography apparatus that avoids possible binding problems when being adjusted for use.

It is also an object of the invention to provide variable column length chromatography apparatus having provisions for avoiding problems with the column packing material.

It is also an object of the invention to provide chromatography apparatus having provisions for eliminating gases from liquid located in its interior.

BRIEF DESCRIPTION OF THE DRAWINGS

The invention will be hereinafter more fully described with reference to the accompanying drawings in which:

FIG. 1 is a top plan view of the chromatography apparatus of the invention;

FIG. 2 is a sectional view of the chromatography apparatus illustrated in FIG. 1 taken on the line 2—2 thereof with certain parts illustrated in an exploded view configuration for clarity;

FIG. 3 is an enlarged view of a portion of the structure illustrated in FIG. 2 taken within the circle 3 thereof;

FIG. 4 is an enlarged view of a portion of the structure illustrated in FIG. 2 taken in the direction of the line 4—4 thereof;

DETAILED DESCRIPTION OF THE PREFERRED EMBODIMENTS

Figure 5:
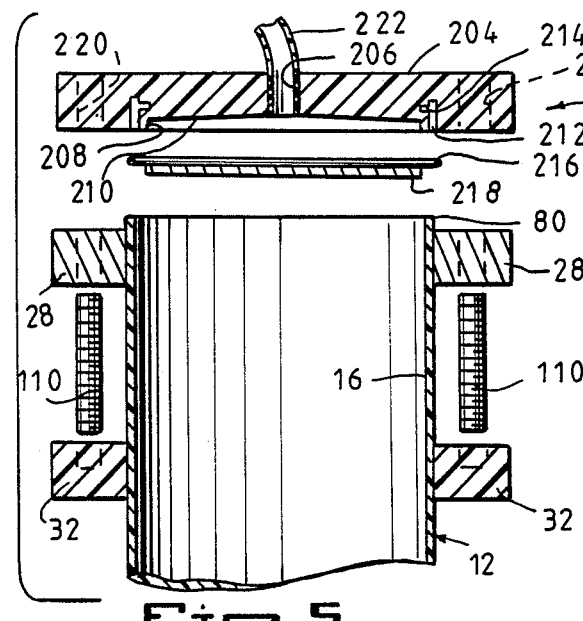
FIG. 5 is a sectional view of a portion of the structure illustrated in FIG. 2 illustrating an alternative structure for the chromatography apparatus of the invention.

Referring first to FIGS. 1 and 2, the chromatography apparatus is illustrated and is designated generally by the number 10. The chromatography apparatus 10 comprises a hollow clear plastic cylinder 12 that has open end portions 14 and 16. The chromatography apparatus 10 also comprises a generally disk shaped end closure plate 18 that closes the open end portion 14 and another closure, plunger plate 20, that closes off the other open end portion 16 and a plunger assembly 22 located within the cylinder 12 that has positioning means 24 connected to it that also passes through the plunger plate 20.

The cylinder 12 has a ring shaped retainer collar 26 located around the outer surface of the open end portion 14 that is securely fastened to the cylinder's outer surface and another ring shaped retainer collar 28 is firmly secured to the outer surface of the open end portion 16. A stud collar ring 30 is located around the outside surface of the end portion 14 of the cylinder 12 inside the retainer collar ring 26 and another substantially identical stud collar ring 32 is located around the outside surface of the end portion 16 of the cylinder 12 inside the retainer collar ring 28. The closure plate 18 has a centrally located threaded hole 34 extending through it from its outside surface 36 to its inner surface 38. The inner surface 38 has a disk shaped depression 40 in it whose bottom surface 42 slopes inward toward the centrally located hole 34 at substantially an angle of two degrees with respect to the flat outside surface 36. A circular ring shaped depression 44 is located in the sloping surface 42 around and in close proximity to the threaded hole 34 and a threaded circular cross section shaped aperture 46 extends from the outer surface 36 to the bottom surface of a portion of the ring shaped depression 44 and is in fluid communication with the depression 44. The threaded apertures 34 and 46 are adapted to be connected to suitable tubes 47 and 48 or other conduits known to those skilled in the art.

Another circular ring shaped depression 50 is located around the hole 34 on the inner surface 38 and is sized and shaped to receive the lip or rim portion 52 of the end portion 14. In addition, a circular shaped channel 54 extends inward toward the hole 34 from the depression 50. This channel 54 is sized and shaped to receive a portion of an O-ring 56 whose purpose is to help make a fluid tight seal between the closure plate 18 and the lip portion 52 when the lip portion 52 is inserted into the depression 50 in the closure plate 18. A series of identical holes represented by the number 58 are located in the outer rim portion of the closure plate 18.

The chromatography apparatus 10 also includes a thin stainless steel sintered disk 60 that is sized and shaped to be securely held in place within the depression 40. This disk 60 has pores located in it that are substantially 0.5 micron in size. The purpose of this disk is to establish and maintain an even liquid distribution radially when the chromatography apparatus 10 is in use. This pore size is important not only to provide proper fluid distribution but also to provide a desirable filtering effect so that the disk 60 filters out undesired foreign substances such as dust.

The closure plate 18 is secured to the end portion 14 of the cylinder 12 by a series of identical threaded attaching studs 62 whose threads are sized and shaped to fit into the threaded holes 64 in the stud ring 30. The projecting portions of the studs 62 then pass through suitably sized identical holes 66 in the retainer collar ring 26 and through the holes 58 in the closure plate 18. Suitably threaded identical nuts 68 are then threaded onto the projecting end portions of the studs 62 so that the stud collar ring 30, the retainer collar 26, and the closure plate 18 are firmly secured together with the lip portion 52 of the cylinder 12 securely in place in the ring shaped depression 50 with the O-ring 56 that is located in the channel 54 pressing outward against the inside surface of the lip portion 52.

The plunger plate 20 has a ring shaped depression 76 located in its inner surface 78 that is similar to the depression 52 that is sized and shaped to receive the lip portion 80 of the end portion 16 of the cylinder 12. The plunger plate 20 has a centrally located threaded aperture 82 that extends from the inner surface 78 to the outer surface 84 that is sized and threaded to receive the threaded plunger shaft 86. The plunger plate 20 also has an unthreaded hole 88 extending form its inner surface 78 to its outer surface 84 that is sized to loosely receive a flexible tube 90 that passes through it. Another threaded hole 92 is located in the inner surface 78 of the plunger plate 20 that is sized and threaded to receive the threaded fitting 94 that is attached to the end of a flexible tubing 96. Another aperture 98 is in fluid communication with the hole 92 and extends radially outward within the plunger plate 20. This aperture 98 is in fluid communication with a larger threaded hole 100 located in the outer rim surface of the plunger plate 20 that is threaded to receive the threaded relief valve 102.

The plunger plate 20 is secured to the end portion 16 of the cylinder 12 in a manner similar to the closure plate 18 and the end portion 14. In this connection, suitably sized holes 104 and 106 are provided in the rim portion of the closure plate 20 and the retainer collar 28. Threaded holes 108 are provided in the stud collar ring 26 that receives the studs 110 that pass through the holes 106 and 104 and receive the threaded nuts 112 that secure the plunger plate 20, the retainer collar 28, and the stud collar ring 32 together with the lip portion 80 firmly located in place in the ring shaped depression 76 in the plunger plate 20.

As illustrated in FIG. 2, the upper end portion 113 of the plunger shaft 86 is threaded into a threaded hole 114 in the generally cylindrical shaped handle hub portion 116. This hub portion 116 has radially outward extending circular cross section shaped holes 118, 120, and 122 in it that are sized and shaped to securely receive the inner end portions 124, 126, and 128 of outward projecting handles 130, 132, and 134. When these handles 130, 132, and 134 and the connected hub portion 116 are rotated in the clockwise direction indicated by the arrows A in FIG. 1 this causes the connected threaded shaft 86 to rotate in the same clockwise direction which causes the shaft to move inward or in the direction of the arrow B in FIG. 2 since the threaded shaft 86 is threaded into the threaded hole 84 in the plunger plate 20.

The plunger assembly 22 in FIG. 2 is also illustrated in greater detail in FIG. 3 and as illustrated the plunger assembly comprises a generally cylindrical shaped piston member 136 that is secured to a generally cylindrical shaped hollow adapter housing 138 that is in turn connected to the lower end portion 140 of the plunger shaft 86 that forms part of the plunger assembly 22 positioning means 24 by a ball and socket joint 142 or similar joint that will permit the plunger shaft 86 to rotate without transmitting the rotation to the adapter housing 138 or the plunger piston member 136. The ball and socket joint 142 also permits the central axis C of the piston member 136 to rotate to form an angular relationship designated by the letter X with the long central axis D of the threaded shaft 86. Consequently, the ball and socket joint 142 prevents the piston member 136 from binding against the inside surface 144 of the cylinder 12 and the piston member is being pushed into the cylinder 12 under the action of the plunger shaft 86 as it moves in the direction of the arrow B.

As illustrated in FIG. 2, the lower end portion 146 of the flexible tube 90 passes through a circular shaped hole 148 in the outer surface portion 150 of the hollow adapter housing 138 and its open end portion 152 is secured in place in the circular shaped hole 154 in the center portion of the piston member 136 through an appropriate glue or the like known in the art. In addition, the open end 156 of the lower portion 158 of the flexible tube 96 is secured in place in a circular shaped hole 160 located in the outer portion of the piston member 136 and a portion of the adjacent rim 162 of the adapter housing 138 through the use of a suitable glue or the like known in the art.

Further details of the plunger assembly 22 and associated structure are best illustrated in FIG. 3. As illustrated in FIG. 3, the ball and socket joint 142 comprises a socket portion 164 that also serves as the ball and socket joint 142 housing. This socket portion 164 surrounds and is in rotational contact with a ball 166 that is formed on the end of the end portion 140 of the plunger shaft 86. The inner portion of the socket joint socket portion has a cylindrical shaped threaded projection 168 that is sized and shaped to be threaded into the threaded hole 170 located in the central portion of the outer portion 150 of the adapted housing 138.

As illustrated in FIG. 3, the adapter housing 138 is secured to the piston member 136 by a series of bolts as represented by the bolt 172 that is sized and shaped to pass through a hole 174 in the rim portion 162 of the adapter housing 138 and be threaded into the adjacent threaded hole 176 in the outer portion of the piston member 136. It will be noted that the inner end of the hole 160 in the piston member 136 is in fluid communication with a slightly smaller hole 178 that extends to the inner surface 180 of the piston member 136 so that fluid can pass from the surface 180 through the hole 178, the hole 160, and into the flexible tube 96.

As also best illustrated in FIG. 2, the threaded hole 154 in the piston member 136 has its inner end in fluid communication with a slightly smaller hole 182 that extends to the center portion of the bottom surface 184 of a generally circular shaped depression 186 located in the inner surface 180 of the piston member 136. It will be noted that this bottom surface has a substantially two degree slope in relationship to the flat inner surface 180 of the piston member 136. The depression 186 is sized and shaped to receive and snugly hold a flat circular shaped stainless steel sintered disk 188 that has substantially a .5 micron pore size. This disk 188 serves to distribute liquid radially and to also filter the liquid.

FIGS. 2 and 3 illustrate that the piston member 136 has both an inner circular groove 190 in the outer cylindrical surface 192 of the piston member 136 and another outer substantially identical circular groove 194 located in the same cylindrical surface 192. Both of these grooves 190 and 194 have a substantially rectangular shaped cross section and the grooves 190 and 194 are sized and shaped to receive the respective substantially identical O-rings 196 and 198 that have a generally circular shaped cross section. These O-rings 196 and 198 contact the inner wall 144 of the cylinder 12 when the piston member 136 is located within the cylinder 12. The use of the two O-rings 196 and 198 provide advantages over previous one ring designs since binding is prevented by the use of two O-rings 196 and 198. Also, the use of the O-ring 196 near the inner surface 180 prevents objects from lodging between the inner portion of the piston member 136 and the inner surface 144 of the cylinder 12 as the piston member 136 moves within the cylinder 12.

Certain details of the central inner portion of the closure plate 18 are illustrated in greater detail in FIG. 4 where an enlargement of a portion of the inner sloping surface 42 of the closure plate 18 is illustrated. The ring shaped depression or groove 44 is located substantially concentrically around the hole 34 in the center of the closure plate 18 and the bottom surface 200 of this groove 44 is connected at one point to the hole 46 so that the groove 44 is in fluid communication with the hole 46. The combination of the centrally located ring shaped groove 44, the sloping surface 42 that slopes toward the groove 44 and the hole 46 provide the closure plate 18 with means for removing bubbles of air or other gases from inside the cylinder 12 when the chromatography apparatus 10 is being used.

To remove bubbles the closure member 18 is oriented so that the bottom surface 200 of the groove 44 is located upward. Bubbles of air or other gases then move upward, due to the effects of gravity, along the surface 42 toward the circular ring shaped groove 44. This ring 44 traps the bubbles since the bubbles move into the ring and upward toward its bottom surface 200 rather than be able to continue upward along the surface 42 to the hole 34. As the bubbles accumulate against the bottom surface 200 they can be drawn off through the hole 46 and the conduit 48 that is connected to and is in fluid communication with the hole 46. It is very important to note that the circular ring shaped depression 44 is continuous and is uninterrupted except for the venting or outlet hole 46. This is important since other interruptions, such as intersecting grooves, etc., could allow bubbles to bypass the groove 44 and hence not be trapped in the groove 44. This would render the ring shaped groove 44 ineffective.

An additional embodiment of the chromatography apparatus 10 previously illustrated in and described with respect to FIGS. 1 through 4 is set forth in FIG. 5 and is designated generally by the number 202. The chromatography apparatus embodiment 202 is identical to the previously described chromatography apparatus 10 except that the apparatus 202 has no provisions for the previously described plunger assembly 22, the positioning means 24, and the plunger plate 20. The open end portion 16 of the cylinder 12 is the same with the same retainer collar 28 and associated stud collar ring 32. The same studs 110 are also used along with the associated nuts 112. However, with the apparatus 202 these studs and associated nuts 112 are used to secure a closure plate 204 rather than the plunger plate 20 of the previously described chromatography apparatus 10.

As illustrated in FIG. 5, the closure plate 204 is substantially similar to the previously described closure plate 18 of the chromatography apparatus 10 except that the circular shaped ring 44 and associated hole 46 have been omitted. In this connection, the closure plate 204 has a centrally located threaded hole 206, disk shaped depression 208 with its sloping bottom surface 210 that slopes at substantially a two degree angle that are similar to those of the closure plate 18. The closure plate 204 also has a circular ring shaped depression or groove 212 and an associated inward extending channel 214 that receive the lip portion 80 of the cylinder 12 and an O-ring 216 that helps form a seal in a manner similar to that for the previously described closure plate 18. A sintered stainless steel disk 218 with a 0.5 micron pore size fits in and is tightly held by the depression 208. This disk is substantially the same as the disk 60. The closure plate 204 has a series of holes 220 that receive portions of the studs 110 so that the closure plate 204 is secured to the end portion 16 of the cylinder 12. A suitable liquid transfer tube 222 is also connected to the hole 206.

Figure 6:
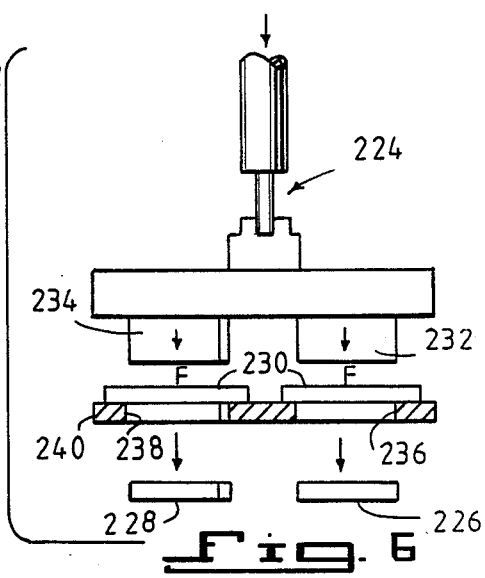
FIG. 6 is a front elevational view of a press being used to carry out a portion of the method of the invention.
Figure 7:
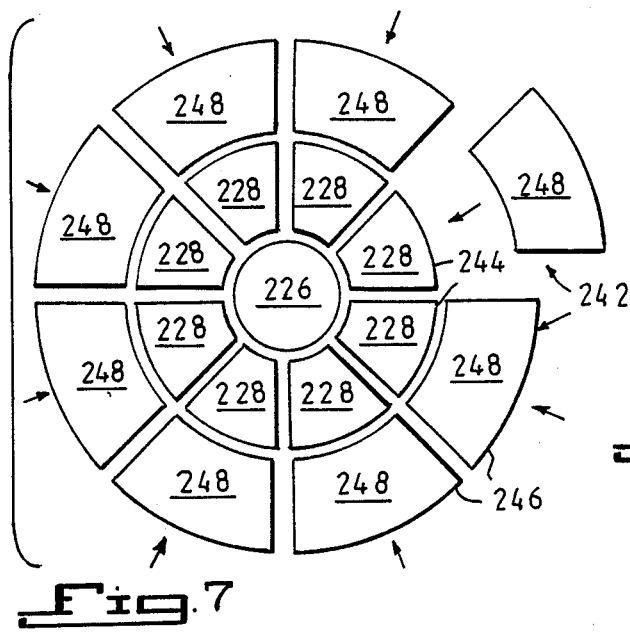
FIG. 7 is a top plan view of a liquid distribution disk being assembled through the method of the invention.
Figure 8:
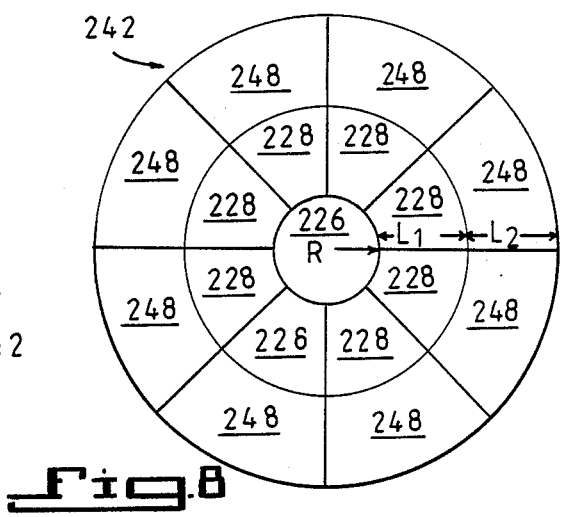
FIG. 8 is a top plan view of the disk structure illustrated in FIG. 7 in its assembled condition.

FIGS. 6 through 8 illustrate the method for manufacturing a liquid distribution disk similar to the previously described disks 60, 188, and 218. In FIG. 6 a front view of a conventional die press is set forth and is designated generally by the number 224. The die press 224 is shown in use stamping out portions 226 and 228 of a stainless steel sintered disk from sintered stainless steel blanks 230. These disk portions 226 and 228 are formed when the die members 232 and 234 move downward in the direction of the arrows F and push a portion of the blanks 230 through the apertures 236 and 238 in the die plate 240. These disk portions 226 and 228 are then appropriately machined in a conventional manner to the required tolerances. It will, of course, be appreciated that other forming techniques known in the art may be substituted for the die press 224.

After the disk portions 226 and 228 are formed as illustrated in FIG. 6 they are then assembled along with other similarly manufactured disk portions as illustrated in FIG. 7. As illustrated, the disk portion 226 is circular shaped and forms the center of a larger composite or segmented disk designated generally by the number 242. The composite segmented disk 242 is assembled by assembling a first concentric ring 244 that consists of a series of adjacently located identical disk portions 228 around the circular center disk portion 226. The next step is to assemble a second concentric ring 246 around the first concentric ring 244. This ring 246 consists of a series of adjacently located identical disk portions 248.

The assembled disk 242 is illustrated in FIG. 8 and as illustrated twice the radius R of the center circular portion 226 is substantially equal to the length L, of the straight side of the segment 228. In addition, the length $L_1$ is substantially equal to the length $L_2$ of the straight side of the segment 248. It should be noted that more than two concentric rings could be used to form the composite segmented disk. However, the lengths L of the straight side of these additional segments would be substantially equal. Consequently, the relationship of the segments of a composite segmented disk would be given substantially by the following equation:

$$2R = L_1 = L_2 = L_n$$

where:

R is the radius of the center segment.

$L_1$ is the length of the straight side of a segment in the first concentric ring.

$L_2$ is the length of the straight side of a segment in the second concentric ring.

$L_n$ is the length of the straight side of a segment in nth concentric ring.

Figure 9:
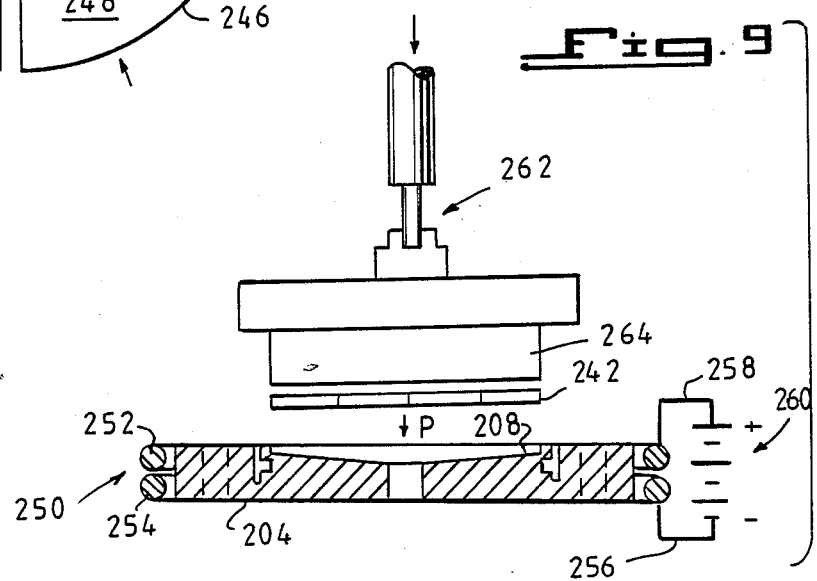
FIG. 9 is a front elevational view of a press being used to make a part of the invention by pressing the assembled disk of FIG. 8 into a preheated end plate.

FIG. 9 illustrates how the assembled disk 242 is pressed into place in a securing member prior to the disk 242 being used. As illustrated, heater 250 with heating coils 252 and 254 is located around a disk 242 securing member which in this case is the closure plate 204. The heating coils 254 and 252 are connected by leads 256 and 258 to a source of electrical heating power 260. A press represented generally by the number 262 is also provided and is located so that its press plate 264 is adjacent the depression 208 in the closure plate 204.

Heating power is then applied to the heater 250. Then when the closure plate 204 is suitably heated by the heater 250 so that the diameter of its depression 208 has sufficiently enlarged, the press 262 is activated and the pressure plate 264 pushes downward in the direction P to push the adjacently located disk 242 into the depression 208. Then the heater 250 is turned off so the plate 204 cools so that the diameter of its depression 208 shrinks so that the rim of the depression 208 tightly secures the disk 242 in the depression 208. The closure plate 204 with the disk 242 secured in it is assembled as part of the apparatus set forth in FIG. 5 in the previously described manner.

It should be noted that even though the disk 242 is made from a number of segments such as the segments 226, 228, and 248 all of these segments are made from the same sintered stainless steel with substantially a 0.5 micron pore size. The segmented composite disk such as the disk 242 can also contain more rings or less rings than those shown in FIGS. 7 and 8 with respect to the disk 242. The number will be chosen by those skilled in the art by the desired size for the disk along with other factors known in the art. The composite, segmented disk such as the disk 242 can be substituted for the previously described disks 60, 188 and 218. In general, the segmented composite type disk 242 or the like will be used for the larger size disks whereas the single piece non-segmented disks 60, 188 and 218 would be smaller in size.

The chromatography apparatus 10 and 202 . are made and used in the following manner. The cylinder 12 and its retainer collars 26 and 28 are made in the preferred embodiment from polycarbonate using suitable forming and machining techniques known in the art. The stud collars 30 and 32 and the closure plates 18 and 204 are made from polypropylene using suitable forming and machining techniques known in the art. The plunger plate 20 is machined from aluminum in a conventional manner as is the handle hub 116 and the handles 130, 132, and 134. The piston member 136 and the adapter housing 138 are also made from aluminum in a conventional manner known to those skilled in the art. The studs 62 and 110 as well as the plunger shaft are made from conventional stainless steel threaded bar stock. The socket portion 164 of the ball joint 142 is conventionally made from swaged and machined aluminum. The various liquid distribution disks 60, 188 and 218 as well as the various segments of the composite disk 242 are made from sintered slab 316 stainless steel 0.5 micron pore size stock by machining and in the case of the disk 242 in the previously indicated manner. The other items that are used to construct the chromatography apparatus 10 and 202 such as the tubing and nuts and bolts, etc. are conventional and readily obtainable.

The chromatography apparatus 10 and 202 are used in a conventional manner similar to any other column chromatography apparatus. In this connection, the interior of the cylinder 12 is packed with a conventional chromatography packing material such as aluminum oxides, cellulose powders and various kinds of anionic and cationic exchange resins or other such materials known in the art. In view of the movable piston member 136 the packing process with the chromatography apparatus 10 is less critical than with the chromatography apparatus 202. With the chromatography apparatus 10, after the cylinder 12 has been packed the piston member 136 is inserted into the open end portion 16. Then the plunger plate 20 is secured in place using the studs 110 and the nuts 112. The piston member 136 can then be moved into place by rotating the handle members 130, 132, and 134 that cause the hub 116 and the connected plunger shaft 86 to rotate and hence move the piston member 136.

The desired liquid can be introduced into the cylinder 12 through the flexible tube 90 where the fluid passes through the sintered disk 188 that distributes the fluid radially and also filters it. During this filling, air can be vented through the flexible tube 96. By suitably orienting the chromatography apparatus 10, bubbles of air and the like remaining in the cylinder 12 can be removed by trapping them in the bubble ring 44 and then venting the trapped air, etc. through the tube 48. The liquid that passes through the packed cylinder 12 then can leave through the tube 47. Alternatively, the tube 47 can be used as the inlet tube and the tube 90 as an exit tube. In this case the sintered disk 60 would appropriately distribute the inlet liquid outward in a radial direction. The chromatography apparatus 202 is used in a manner similar to the apparatus 10. However, there is no piston member 136 and associated structure. Instead, liquid would pass into or leave the cylinder 12 through the tube 222 and the sintered disk 218 would distribute the liquid in a radial direction.

The chromatography apparatus 10 and 202 overcomes previous problems associated with non-uniform distribution of a fluid and inability to properly scale up the apparatus. In addition, the apparatus 10 and 202 permit the ready removal of bubbles and the apparatus 10 and 202 can be readily used for very large scale units.

Although the invention has been described in considerable detail with reference to certain preferred embodiments, it will be understood that variations and modifications may be made within the spirit and scope of the invention as defined in the appended claims.

What is claimed is:

1. Liquid chromatography apparatus comprising an elongated hollow member having two open end portions for receiving a chromatography packing or filling material and end closure means for closing an end of said elongated hollow member having a centrally located aperture for a conduit, said end closure means having means for separating a gas from a liquid comprising an inclined surface and a centrally located substantially uninterrupted ring shaped groove located in said inclined surface close proximity to and around the centrally located conduit aperture with a substantial portion of the inclined surface sloping inward toward said substantially uninterrupted ring shaped groove and the central portion of said closure means and means in fluid communication with said substantially uninterrupted ring shaped groove for drawing off gases from said substantially uninterrupted ring shaped groove, a disk to establish and maintain even liquid distribution radially, and means to vary the position of an end closure means to vary the size of a bed of said packing or filling material.

2. The liquid chromatography apparatus of claim 1 wherein the juncture of said ring and said adjacent sloping surface is substantially uninterrupted.

3. The liquid chromatography apparatus of claim 1 further comprising liquid distribution means located adjacent said end closure means and wherein said liquid distribution means comprises a segmented disk comprising a substantially circular shaped unitary center segment portion surrounded by a plurality of concentric rings with each ring being formed by substantially identical disk portions.

4. The liquid chromatography apparatus of claim 3 wherein the substantially identical disk portions each have straight sides extending from the inner surface to the outer surface of a concentric ring and wherein the radius of the center segment is related to the length of the straight sides of the substantially identical disk portions by the following equation:

$$2R = L_1 = L_2 = L_n$$

where:
  R is the radius of the center segment,
  $L_1$ is the length of the straight side of a segment in the first concentric ring,
  $L_2$ is the length of the straight side of a segment in the second concentric ring, $L_n$ is the length of the straight side of a segment in the nth concentric ring.

5. The liquid chromatography apparatus of claim 1 further comprising a movable piston member located within said elongated hollow member, means for varying the location of said piston member including a shaft, and means connected to said shaft comprising a ball joint for preventing binding of said piston member.

* * * * *